(12) United States Patent
Koshiol et al.

(10) Patent No.: US 6,321,117 B1
(45) Date of Patent: Nov. 20, 2001

(54) CHANGE LOG FOR IMPLANTABLE MEDICAL DEVICE

(75) Inventors: Allan T. Koshiol, Lino Lakes; LeAnne Marie Mackey, St. Louis Park, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/378,104

(22) Filed: Aug. 20, 1999

(51) Int. Cl.[7] .................................................. A61N 1/362
(52) U.S. Cl. ................................................. 607/59; 607/30
(58) Field of Search ................................. 607/27–31, 59

(56) References Cited

U.S. PATENT DOCUMENTS

| | | |
|---|---|---|
| 4,197,850 | 4/1980 | Schulman et al. . |
| 4,232,679 | 11/1980 | Schulman . |
| 4,236,524 | 12/1980 | Powell et al. . |
| 4,407,288 | 10/1983 | Langer et al. . |
| 4,958,632 | 9/1990 | Deggan . |
| 5,309,919 | 5/1994 | Snell et al. . |
| 5,759,199 | 6/1998 | Snell et al. . |
| 5,891,043 | 4/1999 | Ericksen et al. . |
| 6,007,493 | 12/1999 | Ericksen et al. . |
| 6,101,415 | * 8/2000 | Er et al. ................................. 607/27 |

* cited by examiner

Primary Examiner—George R. Evanisko
(74) Attorney, Agent, or Firm—Schwegman, Lundberg, Woessner & Kluth, P.A.

(57) ABSTRACT

A method and system for recording changes to programmable parameters in an implantable pulse generator. An executable program is stored in an implantable pulse generator. A parameter log is maintained in the implantable pulse generator, where the parameter log is used to record changes to the state of one or more programmable parameters of the executable program. When a change is detected in the state, from a first state to a second state, of the one or more programmable parameters the first state of the one or more programmable parameters changed to the second state are recorded in the parameter log. The parameter log is retrievable to allow for analysis of when and how changes took place to the executable program.

20 Claims, 3 Drawing Sheets

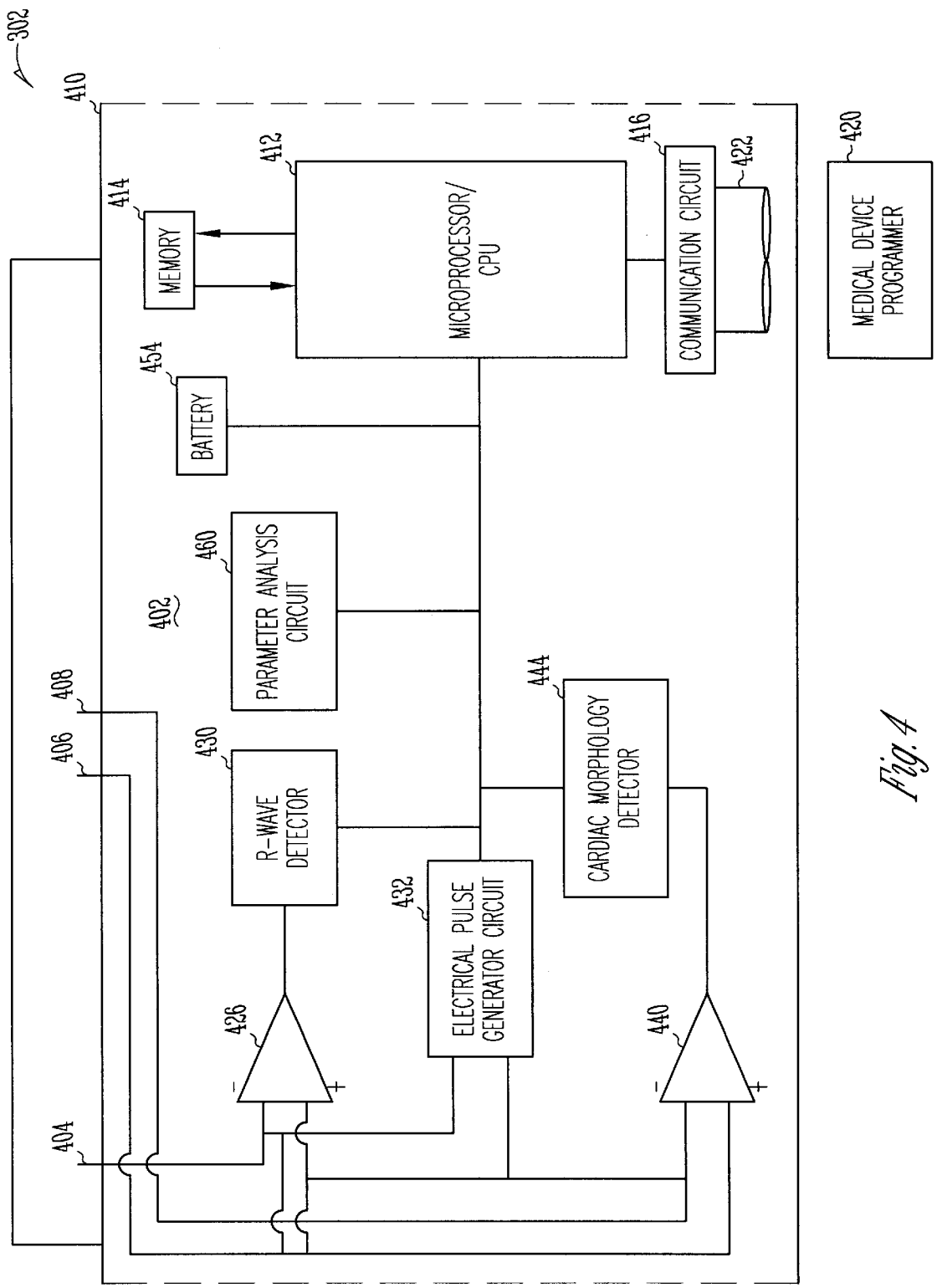

CHANGE LOG FOR IMPLANTABLE MEDICAL DEVICE

FIELD OF THE INVENTION

This invention relates generally to the field of medical devices, and more particularly to implantable medical devices.

BACKGROUND

Cardiac rhythm management devices such as pacemakers, cardioverter/defibrillators, and combination devices typically include numerous program parameters that affect device function, including arrhythmia detection and therapy delivery. Device function can be adjusted to meet the needs of a patient by changing the program parameters. Some examples of program parameters include tachy mode (for detecting and providing therapy for tachycardia) and brady mode (for detecting and providing therapy for bradycardia). Changing program parameters such as tachy mode and/or brady mode activates or deactivates major cardiac analysis and therapy functions of the device.

Most program parameters are adjusted using an external programmer recorder/monitor that communicates with the implanted device via wireless telemetry through the skin. Program parameters may be turned on or off through the use of the external programmer. Other mechanisms may also modify parameter programming. For example, the device may, upon detection of an exhausted battery condition, disable some device functions rather than delivery compromised therapy that may be erratic or potentially dangerous. Some devices respond to the presence of a magnet by inhibiting therapy momentarily, or permanently via magnet maneuvers. Robust device designs perform periodic system integrity validation including program parameters. The device may alter programming to correct integrity errors. These types of changes to the program parameters may have a profound effect on the overall operation of the implanted device.

When a patient visits their physician for routine periodic device follow-ups, the device is interrogated using the external programmer recorder/monitor. During this interrogation, a review is made of parameter programming to assure that the device settings are appropriate for the patient cardiac condition. When parameters are not as expected (e.g., a program parameter has been turned off, or there is an alteration in programmable values the program parameter is using), the clinician must investigate to discover how and why this occurred and take corrective action. Knowing why and when the parameter programming changed is important information to assess the situation. When this information is limited or incomplete, it places doubt on the assessment and the reliability of the device. Therefore, a need exists for understanding how and why parameter programs have been affected during the operation of a cardiac rhythm management device.

SUMMARY OF THE INVENTION

As explained in detail below, the present subject matter is directed to a method and system for providing a log maintained within an implantable medical device that records changes to the operation of the implantable medical device. The log includes entries made by the implantable medical device when operating parameters for executable programs within the medical device and/or the operating state of the implantable medical device change. Logging these types of changes are important in diagnosing how and why changes occurred in the operation of the implantable medical device.

In one embodiment of the present subject matter, an executable program is stored in an implantable pulse generator. The executable program includes one or more programmable parameters that have a first state. The implantable pulse generator further includes a parameter log. The parameter log is used to record changes to the state of the programmable parameters for the executable program. Changes to the state can include turning the executable program on or off, or making alterations to programmable values used by the executable program. When these types of changes are detected, the first state of the one or more programmable parameters changes to a second state. The first state of the one or more programmable parameters changed to the second state is then stored in the parameter log. Then, when it is discovered that changes have occurred to the programmable parameters, the log of these changes can be reviewed by the physician to more easily discover how and why the changes occurred.

Changes recorded in the log include changes to the execution (e.g., turned on or turned off) of the programs for the programmable parameters. Additionally, recorded changes can include those relating the use of a programmable parameter to deliver a "STAT" shock to a patient. Also, events in which the implantable pulse generator initiates an electronic circuitry reset program to test its circuitry and program settings is also recorded in the log. Additional events logged include when the implantable pulse generator is partially or totally disabled with use of a magnet or when the implantable pulse generator terminated an executable program due to a battery malfunction or expiration. In addition to storing why changes occurred to the programmable parameters, the time and the date of the change to the parameters is also recorded in the log.

BRIEF DESCRIPTION OF THE DRAWINGS

FIG. 4 is a block diagram of an implantable pulse generator according to one embodiment of the present subject matter.

DETAILED DESCRIPTION

Figure 1:
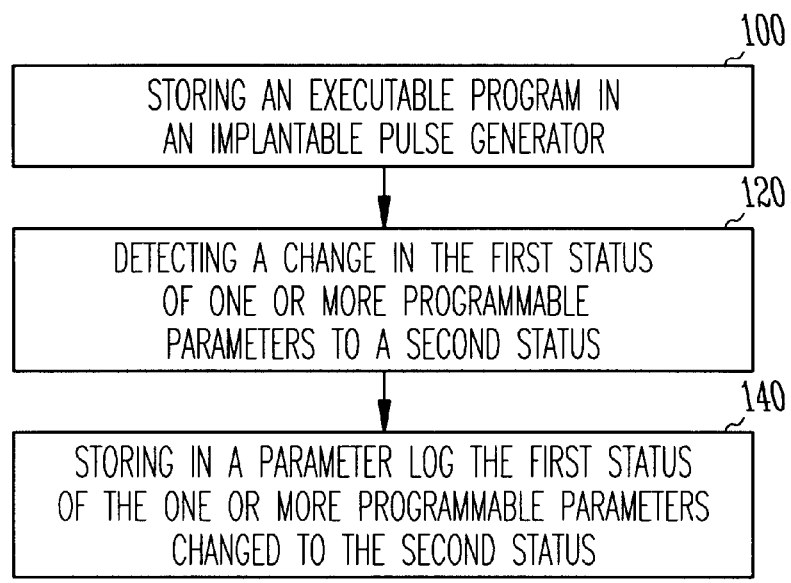
FIG. 1 is a flow chart illustrating one embodiment of the present subject matter.

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

The embodiments of the present subject matter illustrated herein are described as being included in an implantable pulse generator. In one embodiment, the implantable pulse generator is an implantable cardioverter defibrillator, which may include numerous pacing modes known in the art. Alternatively, it is also possible to implement the present subject matter in an implantable cardiac pacemaker.

Furthermore, although the present invention is described in conjunction with an implantable pulse generator having a microprocessor-based architecture, it will be understood that the implantable pulse generator (or other implanted device) may be implemented in any logic based, custom integrated circuit architecture, if desired.

The present subject matter provides for a log to be maintained within an implantable medical device. The log includes entries made by the implantable medical device when operating parameters for executable programs within the medical device and/or the operating state of the implantable medical device change. Logging these types of changes are important in diagnosing how and why changes occurred in the operation of the implantable medical device. For example, an implantable medical device may be programmed to operate in a first state (i.e., a first mode). At a later time, the first state of the implantable medical device is changed due to an external influence, factor and/or signal. This later influencing signal has the effect of changing the operation of the implantable from the first state to a second state. The second state of the implantable device can include changes to the operating parameters of programs being executed within the implantable pulse generator, the termination of programs being executed within the implantable pulse generator, and/or the complete shut-down of the implantable device.

Executable programs are provided within the circuitry of the implantable medical device to direct the operation of the device. Executable programs suitable for controlling and operating implantable pulse generators are known. These programs can include those designed to analyze and provide therapy for bradycardia (e.g., Brady Mode), atrial fibrillation, atrial tachycardia, supraventricular tachycardia, and ventricular fibrillation, congestive heart failure therapy, and other programs intended to treat cardiac arrhythmia and conditions.

A "Tachy Mode" program is an additional example of an executable program implemented in an implantable pulse generator and designed to analyze and provide therapy to treat tachyrhythmia episodes. When the Tachy Mode program is in operation, it analyzes cardiac complexes sensed in one or more sensed cardiac signals to determine the existence of a tachycardia episode and, if programmed to do so, to direct the delivery of therapy to terminate the tachycardia episode. In one embodiment, the state of the Tachy Mode program, or other executable programs, can be altered through the use of a medical device programmer. Altering the state of the Tachy Mode program can be accomplished by delivering one or more signals to the implantable pulse generator. Altering the state of an executable program, such as the Tachy Mode program, can include beginning the execution of the program, terminating (e.g., stopping) the execution of the program, and/or changing programmable parameters associated with the program.

Changes to the state of one or more programs within an implantable pulse generator are logged, or recorded, by the implantable pulse generator when they occur. In one embodiment, the changes logged include the parameter values and/or settings prior to the change in state of the executable program. For example, if at a first time of zero (0) a first parameter of an executable program has a first value. At a second time after the first time (t+0) a change occurs in the value of the first parameter the implantable medical device system logs, or records, the first value of the first parameter. Subsequent changes are also identified and logged by the system. The changes to the state of the executable program can then be reviewed by retrieving the log. Information provided in the log can then be useful in determining how the change occurred, what change occurred, when the change occurred and why the change occurred.

Executable commands, or signals, from a medical device programmer instructing the implantable pulse generator to deliver one or more shocks of electrical energy, such as pacing level pulses, cardioversion and/or defibrillation shocks also initiate changes which are recorded in the log. For example, when a change is initiated in an executable program for the purpose of delivering a "STAT" shock (pacing, cardioversion, and/or defibrillation pulse) the change to the executable program (i.e., executing the program which initially turned off) is logged. Additionally, changes made to an executable program and/or the operation of the implantable pulse generator through the use of a magnetic signal, such as using a magnet, to disable the operation of the implantable medical device are also logged in the implantable pulse generator.

Referring now to FIG. 1, there is shown one embodiment of a method according to the present subject matter. At 100 an executable program is stored in an implantable pulse generator. In one embodiment, the executable program is stored in a memory circuit within the implantable pulse generator and is executed within the electronic circuitry of the implantable pulse generator under the control of a microprocessor. The implantable pulse generator further includes a parameter log. In one embodiment, the parameter log is a list containing the state of an executable program prior to a change in the state of the executable program, when (e.g., time and date) the change to the state occurred along with additional information that will be described in greater detail below.

The executable program stored and executed within the implantable pulse generator includes one or more programmable parameters having a first state. In one embodiment, the first state of the one or more programmable parameters includes being used with the executable program or the state of being not being used when the executable program is terminated (e.g., not executed). At 120, the implantable medical device then analyzes the first state of the one or more programmable parameters to detect a change to a second state of the one or more programmable parameters. In one embodiment, a change in the first state to the second state of the one or more programmable parameters includes a change in the operational status of the executable program as previously discussed.

Once a change is detected, the first state of the one or more programmable parameters changed to the second state is stored in the parameter log at 140. So in one embodiment, the state of the one or more programmable parameters that were actually changed to the second state are logged in the parameter log. The parameter log also is used to record when there is a change to all the one or more programmable parameters, such as when the executable program is (e.g., the Tachy Mode program) either intentionally or accidentally activated or terminated.

In one embodiment, the state of the one or more programmable parameters is changed from a first state to a second state by deactivating the executable program in the implantable pulse generator. Examples of deactivating the executable program include terminating the executable program when the implantable pulse generator receives a magnetic signal. In one embodiment, the magnetic signal is received by a switch coupled to the electronic circuitry of the implantable pulse generator. The change in the state of the programmable parameters is then recorded in the parameter log. In the present example, the termination of the executable program and/or the deactivation of the implantable pulse generator is recorded in the parameter log.

In an additional embodiment, the state of the one or more programmable parameters is changed from a first state to a second state by the exhaustion of the power supply to the implantable pulse generator. For example, implantable pulse generators typically include a battery. When the energy supply from the battery expires, the implantable pulse generator ceases to operate. As a result, executable program(s) within the pulse generator terminate. As this process is occurring, the electronic circuitry within the pulse generator detects the change to the first state to the second state as the executable program ceases to operate. The change in the state of the programmable parameters is then recorded in the parameter log. In the present example, the termination of the executable program and/or the deactivation of the implantable pulse generator is recorded in the parameter log.

Alternatively, the state of the one or more programmable parameters is changed from a first state to a second state by the execution of an electronic circuitry reset program stored in the implantable pulse generator. The change in the state of the programmable parameters is then recorded in the parameter log. In the present example, the execution of the electronic circuitry reset program is recorded in the parameter log. A log of the execution of the electronic circuitry reset program is then stored in the parameter log.

Figure 2:
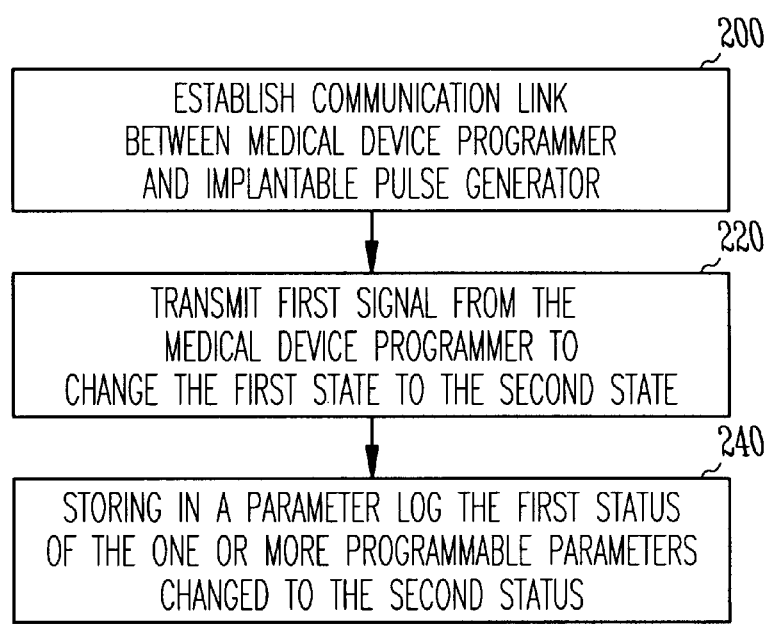
FIG. 2 is a flow chart illustrating one embodiment of the present subject matter.

Referring now to FIG. 2, there is shown an additional embodiment of a method according to the present subject matter. At 200 a medical device programmer is used to establish a communication link between the implantable pulse generator and the medical device programmer. A first signal is then transmitted from the medical device programmer and received by the implantable pulse generator which changes the first state of the one or more programmable parameters to the second state at 220. Once the change is detected, the first state of the one or more programmable parameters changed to the second state is stored in the parameter log at 240.

In one embodiment, the first signal transmitted to and received by the implantable pulse generator controls executable programs contained with the implantable pulse generator. For example, the first signal from the medical device programmer can instruct the electronic circuitry of the implantable pulse generator to terminate running an executable program. Alternatively, the first signal from the medical device programmer can instruct the electronic circuitry of the implantable pulse generator to change one or more programmable parameters used in the execution of an executable program. When these types of changes occur, the values and/or states of the parameters prior to the change are recorded in the parameter log.

In addition to recording changes to the parameter values and/or states, information related to one or more electrical energy shocks delivered under the control of the medical device programmer is recorded in the parameter log. In one embodiment, the medical device programmer is used to generate and transmit a second signal which is received by the implantable pulse generator. The second signal instructs the electronic circuitry of the implantable pulse generator to generate the one or more electrical shocks. In one embodiment, the one or more electrical shocks include pacing level shocks, cardioversion level shocks and/or defibrillation level shocks.

The medical device programmer is also able to transmit a first signal to cause the electronic circuitry of the implantable pulse generator to execute an electronic circuitry reset program. When the electronic circuitry reset program is executed, the first state of the one or more programmable parameters is considered changed and the occurrence of this event is logged in the parameter log. In one embodiment, the electronic circuitry reset program is a hierarchical series of programs which first test the integrity of parameter values and/or states in executable programs. Based on the results of this first test, if the parameter values and/or states are within acceptable ranges the programs designated to be operating are executed. Alternatively, if one or more of the parameter values and/or states are not within acceptable ranges, one or more programs contained within electronic circuitry of the implantable pulse generator attempt to correct the error(s). If this is successful, the programs are executed. If this is not successful, the values and/or states of the parameters are replaced with nominal, or default, settings and the program (s) are executed.

In addition to logging changes in an executable program, executable commands, or signals, from a medical device programmer instructing the implantable pulse generator to deliver one or more shocks of electrical energy, such as pacing level pulses, cardioversion and/or defibrillation shocks are also logged. Furthermore, changes made to an executable program and/or the operation of the implantable pulse generator through the use of a magnetic signal, such as using a magnet, to disable the operation of the implantable medical device are also logged in the implantable pulse generator. Additionally, execution of integrity correction programs within the implantable pulse generator is also recorded in the parameter log.

Also, along with logging changes of state in the parameter values and/or states, additional information is also provided and stored in the parameter log. For example, the additional information provided and stored in the parameter long includes supplying a date and a time when the change in the first state is detected. Additionally, the parameter log maintains a record of a predetermined number of previous changes made to the parameter values and/or state. For example, the predetermined number is a value of at least two (2), where four (4) is an acceptable number. Thus, the first state of the parameters is recorded when a change is detected to a second state. Similarly, the second state of the parameters is recorded when a change is detected to a third state. This type of recording of the state of parameters continues to occur until the parameter log has recorded the predetermined number of changes to the parameters. Additionally, besides storing only the parameters that have changed from one state to a next state, the one or more programmable parameters unchanged from one state to the next state (e.g., from the first state to the second state) are also stored in the parameter log.

In one embodiment, the parameter log stored in the implantable pulse generator is accessible though the use of a medical device programmer. The medical device programmer allows for one or more command signals to be sent to the implantable medical device. Upon receiving the command signals the implantable pulse generator down loads, or transfers, information contained in the parameter log to the medical device programmer. The medical device programmer is then used to view the contents of the parameter log gathered by the implantable pulse generator.

Figure 3:
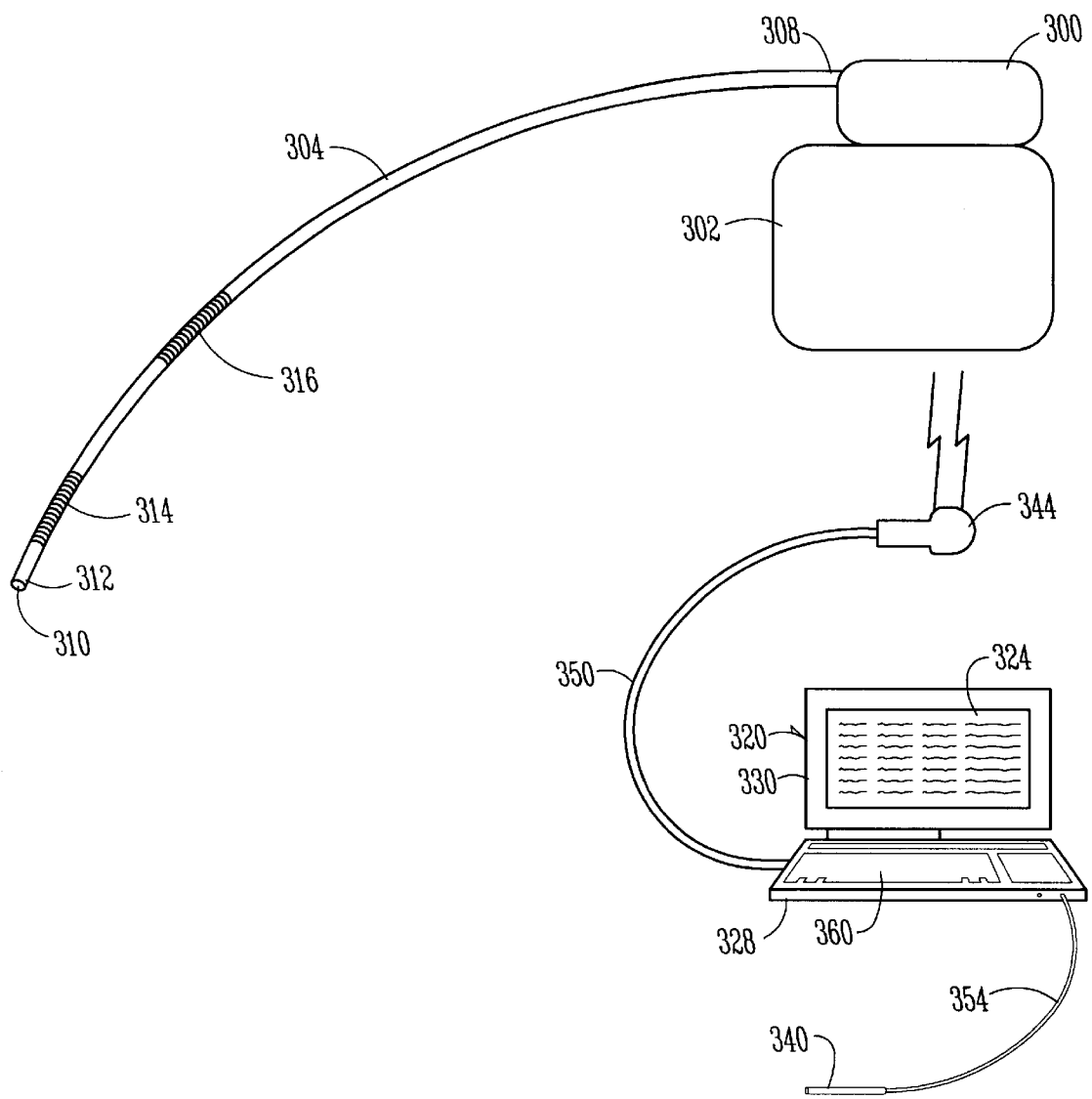
FIG. 3 is a schematic view of an implantable pulse generator and a medical device programmer according to one embodiment of the present subject matter.

Referring now to FIG. 3 of the drawings, there is shown one embodiment of an implantable pulse generator 300. In the present embodiment, the implantable pulse generator 300 is an implantable cardiac defibrillator 302 electrically and physically coupled to at least one intracardiac catheter 304. In one embodiment, the intracardiac catheter 304 includes one or more pacing electrodes and one or more defibrillation electrodes positioned on the intracardiac catheter 304.

The intracardiac catheter 304 is used to sense one or more cardiac signals which contain cardiac complexes each indicative of at least a portion of a cardiac cycle. Electronic circuitry contained within the implantable cardiac defibrillator 302 is used to analyze the sensed cardiac complexes to determine the occurrence of an arrhythmic episode. Based on the analysis of the cardiac complexes in the cardiac signals, the electronic circuitry within the implantable cardiac defibrillator 302 delivers one or more electrical pulses to electrodes on the one or more intracardiac catheters under certain predetermined conditions to treat the arrhythmic episode.

In one embodiment, the intracardiac catheter 304 is an endocardial lead that is releasably attached to the cardiac defibrillator 302. The intracardiac catheter 304 has an elongate body with a proximal end 308 and a distal end 310 and is shown as having a pacing electrode 312 located at, or adjacent, the distal end 310 of the intracardiac catheter 304. In one embodiment, the pacing electrode 312 is a tip electrode positioned at the distal end 310 of the intracardiac catheter 304. Alternatively, the pacing electrode 312 is an annular, or a semi-annular ring electrode positioned adjacent the distal end 310.

The intracardiac catheter 304 also includes one or more defibrillation electrodes. In one embodiment, the intracardiac catheter 304 has a first defibrillation electrode 314 and a second defibrillation electrode 316, where the first defibrillation electrode 314 and the second defibrillation electrode 316 are defibrillation coil electrodes as are known in the art. The first defibrillation electrode 314 is spaced apart and proximal from the pacing electrode 312, and the second defibrillation electrode 316 is spaced apart and proximal from the first defibrillation electrode 314.

Referring now to FIG. 4, there is shown an embodiment of a block diagram of the implantable cardiac defibrillator 302. The implantable cardiac defibrillator 302 includes electronic control circuitry 402 for receiving one or more cardiac signals and delivering electrical energy to the one or more electrodes. The electronic control circuitry 402 includes terminals, labeled with reference numbers 404, 406, and 408 for connection to electrodes attached to the surface of the intracardiac catheter 304. The pacing electrode 312 is electrically connected to terminal 404 and to the electronic control circuitry 402 through an electrically insulated conductor provided within the elongate body of the intracardiac catheter 304. The first defibrillation electrode 314 and the second defibrillation electrode 316 are connected to terminals 406 and 408, respectively, and to the electronic control circuitry 402 through electrically insulated conductors provided within the elongate body of the intracardiac catheter 304.

In one embodiment, the electronic control circuitry 402 of the cardiac defibrillator 302 is encased and hermetically sealed in a housing 410 suitable for implanting in a human body. In one embodiment, titanium is used for the housing 410, however, other biocompatible housing materials as are known in the art may be used. A connector block 412 is additionally attached to the housing 410 of the cardiac defibrillator 302 to allow for the physical and the electrical attachment of the intracardiac catheter 304 and the electrodes to the cardiac defibrillator 302 and the encased electronic control circuitry 402.

The electronic control circuitry 402 of the cardiac defibrillator 302 is a programmable microprocessor-based system, with a microprocessor 412 and a memory circuit 414, which contains parameters for various pacing and sensing modes and stores data indicative of cardiac signals received by the electronic control circuitry 402. In one embodiment, the memory circuit 414 stores the parameter log and one or more executable programs used by the implantable cardiac defibrillator 302 to analyze and treat detected arrhythmic episodes. In addition to storing the one or more executable programs, one or more programmable parameters having a first state are also stored for the executable programs.

A communication circuit 416 is additionally coupled to the electronic control circuitry 402, the memory circuit 414 and the microprocessor 412 to allow the cardiac defibrillator 302 to establish a communication link between the cardiac defibrillator 302 and a medical device programmer 420. In one embodiment, the communication circuit 416 and the medical device programmer 420 use a wire loop antenna 422 and a radio frequency telemetric link, as is known in the art, to receive and transmit signals and data to and from the medical device programmer 420 and the electronic control circuitry 402. In this manner, a first signal, including programming commands and/or instructions, is transmitted from the medical device programmer 420 and received by the communication circuit 416 to change the first state of the one or more programmable parameters to the second state. Additionally, stored cardiac data, including the parameter log, pertaining to sensed arrhythmic episodes are transferred to the medical device programmer 420 from the cardiac defibrillator 302.

The embodiment of the cardiac defibrillator block diagram shows the pacing electrode 304 and the first defibrillation electrode 314 coupled to a sense amplifier 426 to allow for bipolar sensing and pacing. The output of the sense amplifier 426 is shown connected to an R-wave detector 430. These components serve to sense and amplify R-waves, and apply signals indicative thereof to the microprocessor 412. Among other things, microprocessor 412 responds to the R-wave detector 430 by providing pacing signals to an electrical pulse generator circuit 432 coupled to the microprocessor 412, as needed according to the programmed pacing mode. In one embodiment, the electrical pulse generator circuit 432 provides pacing level pulses to terminals 404 and 406, which connect to the pacing electrode 304 and the first defibrillation electrode 314 for bipolar cardiac pacing. Power to the cardiac defibrillator 302 is supplied by an electrochemical battery 454 that is housed within the cardiac defibrillator 302.

The first defibrillation electrode 304 and the second defibrillation electrode 306 are coupled to a sense amplifier 440, whose output is connected to a cardiac morphology detector 444. These components serve to sense and amplify QRS-complexes, and apply signals indicative thereof to the microprocessor 412. In one embodiment, the cardiac morphology detector 444 includes an analog filter for filtering cardiac signal noise sensed by the electrodes. The cardiac signals are then bandlimited before arriving at an analog-to-digital filter. The cardiac signals are then A/D converted into a digital signal and subsequently received by the microprocessor 412. The microprocessor 412 responds to the sensed cardiac signals by providing electrical energy pulses (cardioversion and/or defibrillation pulses) from the electrical pulse generator circuit 432.

In one embodiment, the medical device programmer 420 is used to produce a second signal that when received by the communication circuit 416. Upon receiving the second signal, the microprocessor 412 controls the electrical pulse generator circuit 432 to generate one or more electrical energy shocks. In one embodiment, the one or more electrical energy shocks produced are pacing level shocks. Alternatively, the one or more electrical energy shocks are cardioversion and/or defibrillation level shocks. After a second signal from a medical device programmer has been used to produce electrical energy shocks, the microprocessor 412 stores information related to the one or more electrical energy shocks (e.g., type of shocks delivered, strength of the shocks delivered, etc.) in the device log. Additionally, the second signal instructing the implantable pulse generator to deliver one or more shocks of electrical energy also initiates changes to the programs which are recorded in the log. For example, when a change is initiated in an executable program for the purpose of delivering a "STAT" shock (pacing, cardioversion, and/or defibrillation pulse) the change to the executable program (i.e., executing the program which initially turned off) is logged.

Executable commands, or signals, from a medical device programmer instructing the implantable pulse generator to deliver one or more shocks of electrical energy, such as pacing level pulses, cardioversion and/or defibrillation shocks also initiate changes which are recorded in the log. For example, when a change is initiated in an executable program for the purpose of delivering a "STAT" shock (pacing, cardioversion, and/or defibrillation pulse) the change to the executable program (i.e., executing the program which initially turned off) is logged.

The cardiac defibrillator 302 further includes a parameter analysis circuit 460 coupled to the memory circuit 414, where the parameter analysis circuit 460 analyzes the first state of the one or more programmable parameters to detect a change in a first state to a second state of the one or more programmable parameters. When changes to the programmable parameter states are detected (e.g., the change of one or more programmable parameters from the first state to a second state), the state and/or value of the parameters prior to the change are stored in the parameter log by the microprocessor 412 in the memory circuit 414 which is coupled to both the microprocessor 412 and the parameter analysis circuit 460.

In one embodiment, the first signal received by the communication circuit 416 controls the executable program. For example, the first signal received by the communication circuit 416 can direct the microprocessor 412 to terminate one or more executable programs being performed in implantable cardiac defibrillator 302. Alternatively, the first signal received by the communication circuit 416 changes the status and/or value of programmable parameters used by executable programs in the implantable cardiac defibrillator 302.

The electronic control circuitry of the implantable pulse generator further includes a clock from which both a time and a date are provided to the parameter log. In one embodiment, the clock is included in the microprocessor 412 to provide information relative to time, including the time and the date of when changes in state to the programmable parameters occur. When changes to the parameter state occur, the microprocessor 412 stores the time and the date in the parameter log when the state of the one or more programmable parameters is changed.

Referring again to FIG. 3, there is shown one embodiment of a medical device programmer 320. As previously mentioned, one embodiment of the medical device programmer 320 for the implantable cardiac defibrillator 302 takes the form of an external controller as are known in the art. The medical device programmer 320 is designed to communicate with an implantable medical device, such as the cardiac defibrillator 302, via radio frequency telemetry. The medical device programmer 320 has programmer electronic circuitry, including a microprocessing unit and related circuitry, such as digital memory, which is coupled to a graphics display screen 324.

In one embodiment, the medical device programmer 320 comprises an outer housing 328 which is made of a thermal plastic or other suitable lightweight durable material. The graphics display screen 324 is disposed on the upper surface of housing 330. The graphics display screen 324 folds down into a closed position when medical device programmer 320 is not in use, thereby reducing the size of medical device programmer 320 and protecting the display surface of graphics display screen 324 during transportation and storage.

In an additional embodiment, the external programmer additionally has a floppy disk drive and/or a removable disk drive and a hard drive disposed within the housing. Air vents are provided at various points in the housing so that an internal fan can circulate air within the housing 328 and prevent overheating of components therein.

The medical device programmer 320 is shown with the graphics display screen 324 positioned in one of a plurality of possible open positions such that a display on the graphics display screen 324 is visible to a user situated in front of the medical device programmer 320. In one embodiment, the graphics display screen 324 is of the LCD or electroluminescent type. The graphics display screen 324 is operatively coupled to the electronic circuitry disposed with the housing 328 and is adapted to provide a visual display of graphics and/or data under control of the programmer electronic circuitry.

The medical device programmer 320 further includes a user input device coupled to the electronic circuitry. In one embodiment, the user input device is the graphics display screen 328, which is provided with touch-sensitive capability, such that a user can interact with the programmer electronic circuitry by touching the display area on the graphics display screen 328 with a stylus 340, or even the user's finger. In one embodiment, the touch-sensitive graphics display screen is primary input for the medical device programmer 320. The medical device programmer 320 further includes a programming head 344, which is place over a patient's body near the implant site of an implanted device, such as the cardiac defibrillator 302, in order to establish a telemetry link between the cardiac defibrillator 302 and the medical device programmer 320. The telemetry link between the cardiac defibrillator 302 and the medical device programmer 320 allows the electronic circuitry coupled to the graphics display screen to be coupled to the electronic control circuitry of the cardiac defibrillator 302. The programming head 344 is coupled to the electronic circuitry of medical device programmer 320 and a receiver circuit for receiving signals from the communication circuit indicative of cardiac signals by a cable 350.

The stylus 340 used to interact with the touch-sensitive graphics display screen 324 is coupled to the programmer electronic circuitry within the housing 328 by a cable 354. Alternatively, the medical device programmer 320 may be equipped with a conventional computer "mouse"-type pointing device or a trackball, rather than a stylus. In the absence of either a stylus or a mouse, on-screen cursor control for enabling user interaction with medical device programmer 320 may be facilitated through cursor control keys 360 (arrow keys or the like) disposed on the medical device programmer 320.

The medical device programmer 320 further includes a receiver circuit for receiving signals from the communication circuit indicative of cardiac signals. Through the telemetric contact with the cardiac defibrillator 302, the medical device programmer 320 is capable of capturing and storing recorded electrocardiogram data transmitted from the cardiac defibrillator 302 and displaying the electrocardiogram data on its graphics display screen 324.

This application is intended to cover any adaptations or variations of the present invention. It is manifestly intended that this invention be limited only by the claims and equivalents thereof.

We claim:

1. A method, comprising:

storing an executable program in an implantable pulse generator, wherein the implantable pulse generator includes a parameter log and the executable program includes one or more programmable parameters having a first state;

establishing a communication link between the implantable pulse generator and a medical device programmer;

transmitting a first signal from the medical device programmer to change the first state of the one or more programmable parameters to the second state;

receiving the first signal to change the first state of the one or more programmable parameters to the second state;

detecting the change in the first state of the one or more programmable parameters to the second state; and storing in the parameter log the first state of the one or more programmable parameters changed to the second state.

2. The method of claim 1, wherein transmitting the first signal includes controlling the executable program.

3. The method of claim 2, wherein controlling the executable program includes terminating the executable program; and storing a log of the executable program termination.

4. The method of claim 2, wherein controlling the executable program includes activating the executable program; and storing a log of the executable program activation.

5. The method of claim 1, including generating one or more electrical energy shocks upon the implantable pulse generator receiving a second signal;

storing in the parameter log information related to the one or more electrical energy shocks; and storing a log of the second signal.

6. The method of claim 1, wherein the implantable pulse generator includes an electronic circuitry reset program and transmitting the first signal from the medical device programmer to change the first state of the one or more programmable parameters includes executing the electronic circuitry reset program when the first signal is received.

7. The method of claim 1, including terminating the executable program when the implantable pulse generator receives a magnetic signal;

detecting the change includes detecting when the executable program terminates due to the magnetic signal; and storing a log of the magnetic signal in the parameter log.

8. The method of claim 1, wherein the implantable pulse generator includes a battery, and terminating the executable program when the battery expires;

detecting the change includes detecting when the executable program terminates due to the expired battery; and storing a log of the expired battery in the parameter log.

9. The method of claim 1, including providing additional information to the parameter log; and storing the additional information in the parameter log.

10. The method of claim 9, wherein providing additional information includes supplying a date and a time when the change in the first state is detected.

11. The method of claim 1, including detecting the execution of an electronic circuitry reset program in the implantable pulse generator; and storing a log of the execution of the electronic circuitry reset program in the parameter log.

12. The method of claim 1, including detecting a change in the second state of the one or more programmable parameters to a third state; and storing in the parameter log the second state of the one or more programmable parameters changed to the third state.

13. The method of claim 1, including storing in the parameter log the first state of the one or more programmable parameters unchanged to the second state.

14. The method of claim 1, including detecting an execution of an integrity correction program in the implantable pulse generator; and storing a log of the execution of the integrity correction program in the parameter log.

15. The method of claim 1, comprising sensing a cardiac signal, and changing the one or more programmable parameters based on the sensed cardiac signal.

16. A system including an implantable pulse generator and medical device programmer, the implantable pulse generator including:

a memory circuit to store a parameter log and an executable program, wherein the executable program includes one or more programmable parameters having a first state;

a parameter analysis circuit coupled to the memory circuit, wherein the parameter analysis circuit analyzes the first state of the one or more programmable parameters to detect a change in the first state to a second state of the one or more programmable parameters;

a microprocessor coupled to the memory circuit and the parameter analysis circuit, wherein the microprocessor stores the first state of the one or more programmable parameters changed to the second state in the parameter log; and a communication circuit coupled to the microprocessor, wherein the communication circuit establishes a communication link between the implantable pulse generator and the medical device programmer, and the medical device programmer transmits a first signal, the communication circuit receives the first signal and in response to the first signal the first state of the one or more programmable parameters is changed to the second state.

17. The system of claim 16, wherein the first signal received by the communication circuit controls the executable program.

18. The system of claim 17, wherein the first signal terminates the executable program.

19. The system of claim 16, including an electrical pulse generator circuit coupled to the microprocessor, wherein the medical device programmer produces a second signal received by the communication circuit that causes the microprocessor to control the electrical pulse generator circuit to generate one or more electrical energy shocks, and the microprocessor stores information related to the one or more electrical energy shocks in the parameter log.

20. The system of claim 16, wherein the microprocessor includes an internal clock to provide information relative to time, including a time and a date, and wherein the microprocessor stores the time and the date in the parameter log when the first state of the one or more programmable parameters is changed to the second state.

* * * * *